(12) United States Patent
Stein

(10) Patent No.: US 6,923,784 B2
(45) Date of Patent: Aug. 2, 2005

(54) THERAPEUTIC TREATMENT OF DISORDERS BASED ON TIMING INFORMATION

(75) Inventor: Marc T. Stein, Chandler, AZ (US)

(73) Assignee: Medtronic, Inc., Minneapolis, MN (US)

( * ) Notice: Subject to any disclaimer, the term of this patent is extended or adjusted under 35 U.S.C. 154(b) by 166 days.

(21) Appl. No.: 10/000,638

(22) Filed: Oct. 31, 2001

(65) Prior Publication Data

US 2002/0038137 A1 Mar. 28, 2002

Related U.S. Application Data

(62) Division of application No. 09/303,144, filed on Apr. 30, 1999, now abandoned.

(51) Int. Cl.[7] ............................................. A61M 31/00
(52) U.S. Cl. ........................................... 604/67; 604/65
(58) Field of Search .............................. 604/65, 66, 67, 604/93, 891.1; 128/13, DIG. 12

(56) References Cited

U.S. PATENT DOCUMENTS

| | | | | |
|---|---|---|---|---|
| 4,146,029 A | * | 3/1979 | Ellinwood, Jr. | ............. 128/260 |
| 4,570,640 A | * | 2/1986 | Barsa | ......................... 128/741 |
| 5,113,869 A | * | 5/1992 | Nappholz et al. | ........... 600/508 |
| 5,263,480 A | | 11/1993 | Wernicke et al. | |
| 5,304,206 A | | 4/1994 | Baker, Jr. et al. | |
| 5,683,422 A | | 11/1997 | Rise | |
| 5,702,426 A | | 12/1997 | Pons et al. | |
| 5,711,316 A | | 1/1998 | Elsberry et al. | |
| 5,713,923 A | | 2/1998 | Ward et al. | |
| 5,716,316 A | | 2/1998 | Cartier et al. | |
| 5,716,377 A | | 2/1998 | Rise et al. | |
| 5,735,814 A | | 4/1998 | Elsberry et al. | |
| 5,782,798 A | | 7/1998 | Rise | |
| 5,792,186 A | | 8/1998 | Rise | |
| 5,814,014 A | | 9/1998 | Elsberry et al. | |
| 5,824,021 A | | 10/1998 | Rise | |
| 5,928,272 A | | 7/1999 | Adkins et al. | |
| 6,066,163 A | | 5/2000 | John | |
| 6,475,180 B2 | * | 11/2002 | Peterson et al. | .............. 604/65 |

* cited by examiner

*Primary Examiner*—Manuel Mendez
(74) *Attorney, Agent, or Firm*—Hanner & Witcoff, Ltd.

(57) ABSTRACT

Disclosed are techniques for operation of neurostimulation or drug delivery devices to stop treatment therapy during times when the patient does not need to be treated. Advantageously, the present invention reduces battery usage and/or drug dosage during periods when treatment therapy need not be provided. Further, the present invention slows or reduces the tolerance the patient may develop from the electrical stimulation or treatment therapy. In one embodiment, the present invention includes a timer or a real time clock for shutting off the device during periods when the patient is sleeping in accordance with a preset schedule. The present invention preferably turns off after the patient has fallen asleep and right before the patient has awakened. Alternatively, the invention may include a sensor for sensing conditions indicative of whether the patient is awake or asleep. This sensed information may also be used to determine whether the treatment therapy should be delivered or stopped.

28 Claims, 7 Drawing Sheets

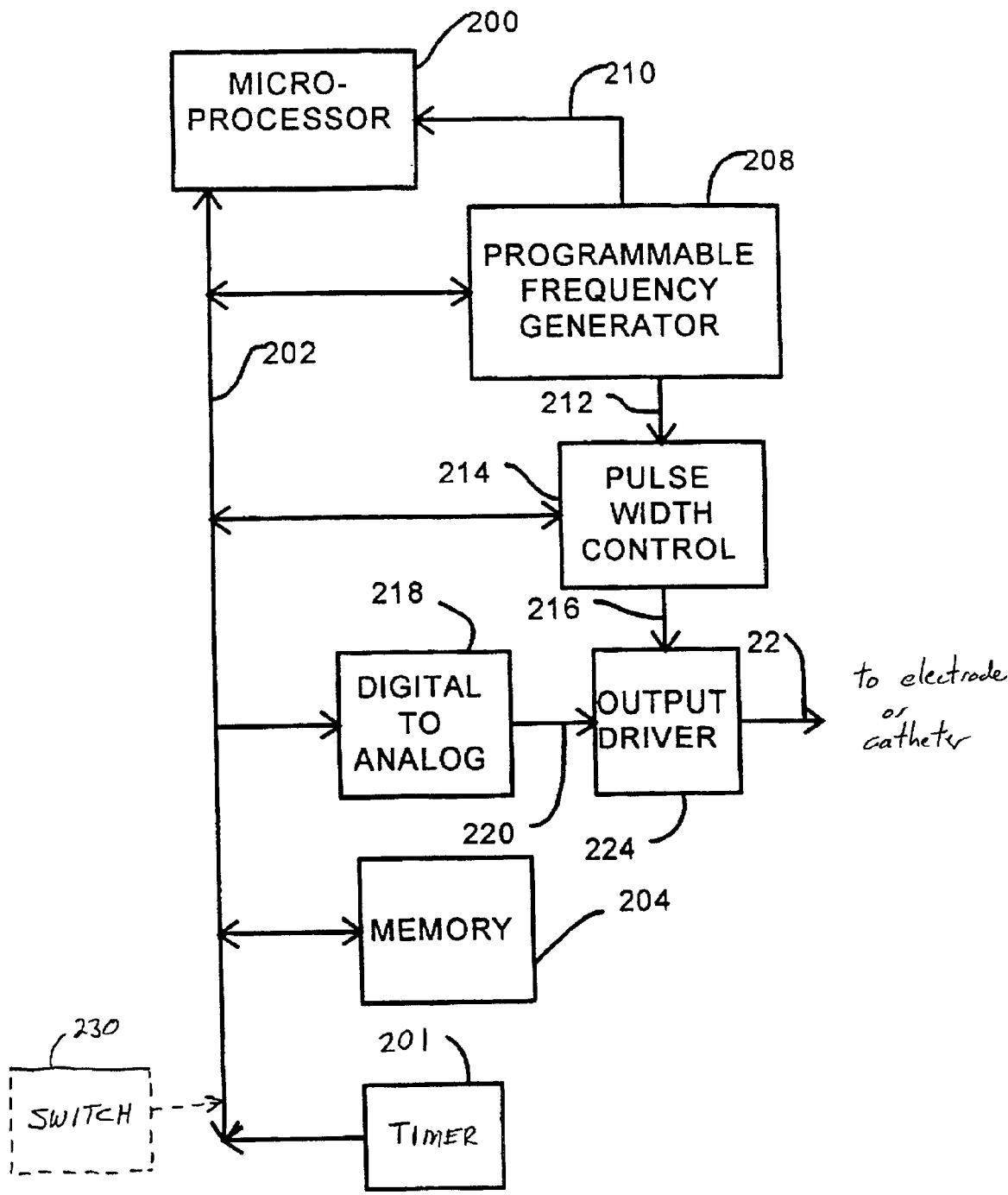

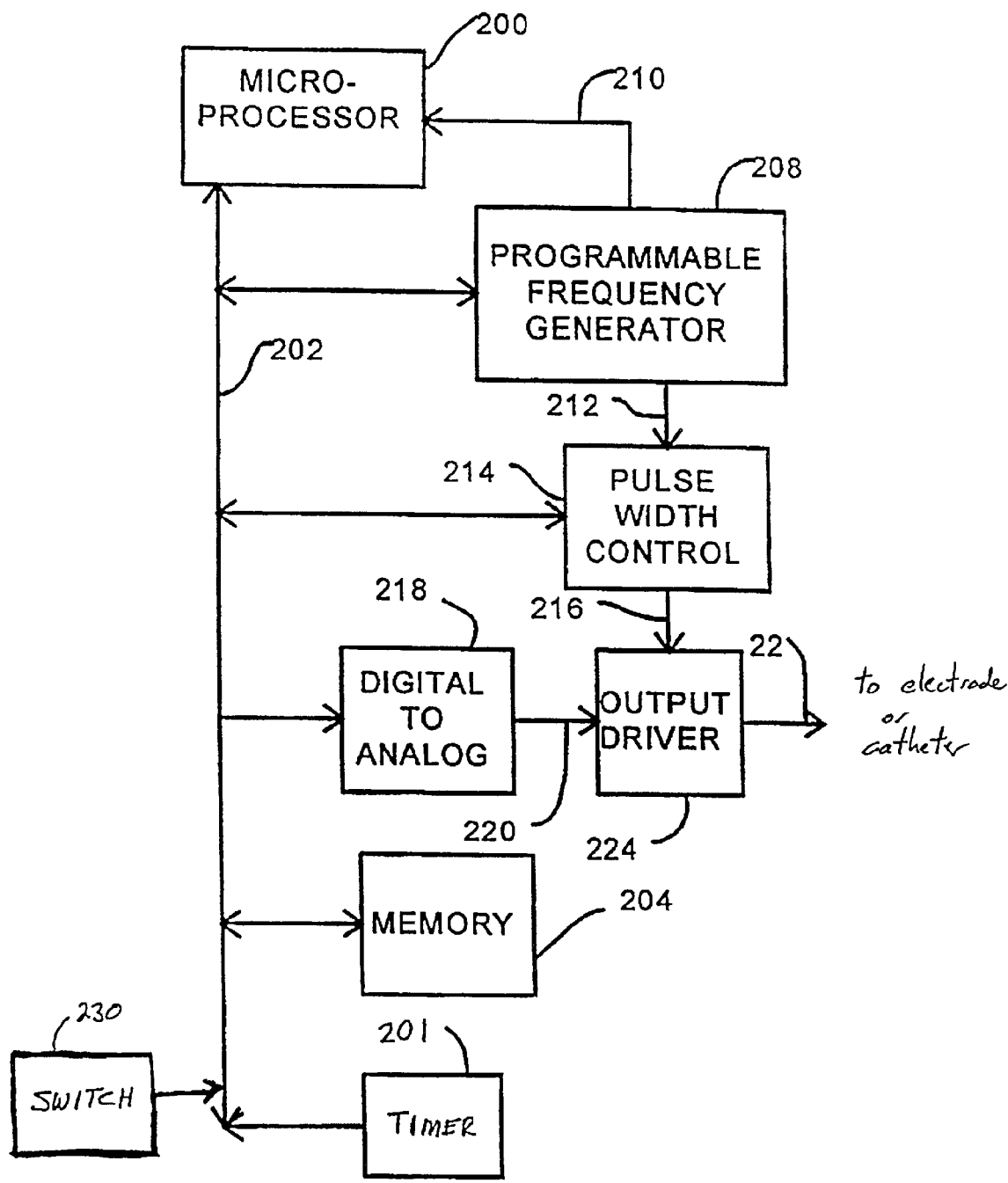

THERAPEUTIC TREATMENT OF DISORDERS BASED ON TIMING INFORMATION

This is a divisional of application Ser. No. 09/303,144, filed Apr. 30, 1999, now abandoned, for which priority is claimed. This parent application is incorporated herein by reference in its entirety.

BACKGROUND OF THE INVENTION

1. Field of the Invention

The present invention relates to neurostimulation or drug infusion devices, and more particularly relates to techniques for activating or deactivating a neurostimulator or drug delivery system based on time-of-day or biological rhythmic patterns.

2. Description of Related Art

Neurostimulation devices and drug delivery devices are now capable of treating any number of disorders as well as symptoms of disorders. In the context of neurostimulators, an electrical lead having one or more electrodes is typically implanted near a specific site in the brain or spinal cord of a patient. The lead is coupled to a signal generator which delivers electrical energy through the electrodes to nearby neurons and neural tissue. The electrical energy delivered through the electrodes creates an electrical field causing excitation of the nearby neurons to directly or indirectly treat the neurological disorder or a symptom of the disorder. In the context of a drug delivery system, a catheter coupled to a pump is implanted near a treatment site in the brain or spinal cord. These systems are commonly implanted within the body and are operated by a power source such as a battery.

Recent advances have allowed these neurostimulation devices and drug delivery systems to adjust treatment in accordance with the patient's needs. Generally, these systems incorporate a sensor for sensing a physical or chemical characteristic of the body and generating a sensor signal in response. The sensor signal may then be used to adjust the treatment therapy. U.S. Pat. No. 5,716,377, for example, discloses a method of treating movement disorders by closed loop brain stimulation.

These systems, however, provide electrical stimulation or drug delivery regardless of the time of day or the patient's needs. These system are capable of adjusting the treatment but are incapable of recognizing periods when a patient does not require any therapy. For example, patients often will not require any stimulation or drug therapy during periods when he/she is resting or sleeping. During such time periods, the manifestation of the movement disorder may be minimal or even non-existent. This is often the case for patients suffering from movement disorders and certain types of pain.

Stimulation or drug delivery at times when it is not required by the patient unnecessarily depletes the battery or the drug reserve which is often implanted within the body. This requires more frequent surgical procedures to replace the spent battery or more frequent drug injections. An even greater concern with continuous therapy systems is that the patient may develop a higher tolerance to the treatment, thereby requiring higher dosage or stronger stimulation to achieve the desired result.

Often, physicians will request the patient to turn off his/her neurostimulator at night. This requires the patient or care giver to manually turn the device off at night before falling asleep and turn on the device after waking up the next day. However, after the neurostimulator is turned off but before the patient has fallen asleep, symptoms of movement disorders, illnesses or other maladies (such as tremor) or pain often return, thereby rendering sleep difficult. Accordingly, there remains a need in the art for automatically shutting off the electrical stimulation or drug delivery during periods when the patient does not require treatment therapy.

SUMMARY OF THE INVENTION

As explained in more detail below, the present invention overcomes the above-noted and other shortcomings of the prior art neurostimulation devices. The present invention provides a technique for shutting off the electrical stimulation or drug delivery during periods when the treatment therapy is not desired. In one embodiment, the neurostimulator has a timer or a clock capable of turning on or off the treatment therapy at predetermined times. Accordingly, the system may be automatically turned off at a time when the patient is usually fast asleep and turned on at a time prior to the patient awakening. In the context of a neurostimulation device, the present invention includes an implantable signal generator, a timer coupled to the signal generator for providing timing information to the signal generator, and circuitry (a microprocessor) within the signal generator for determining whether the signal generator is turned off or on in response to the timer information. Timer may alternatively be a real time clock.

In another embodiment, the present invention includes a sensor coupled to the signal generator for generating a signal indicative of whether a patient is asleep or awake. The microprocessor receives time of day information from the timer and information as to whether the patient is awake or asleep from the sensor. Based on these signals, the microprocessor may automatically initiate or stop the treatment to the patient.

The present invention may also be implemented within an implantable drug delivery system in accordance with the principles of the above-described embodiments.

BRIEF DESCRIPTION OF THE DRAWINGS

These and other advantages and features of the invention will become apparent upon reading the following detailed description and referring to the accompanying drawings in which like numbers refer to like parts throughout and in which:

FIG. 2 is a schematic block diagram of the circuitry of device or signal generator in accordance with a preferred embodiment of the present invention;

FIG. 2A is a schematic block diagram of the circuitry of device or signal generator in accordance with another preferred embodiment of the present invention;

DESCRIPTION OF THE PREFERRED EMBODIMENTS

Figure 1:
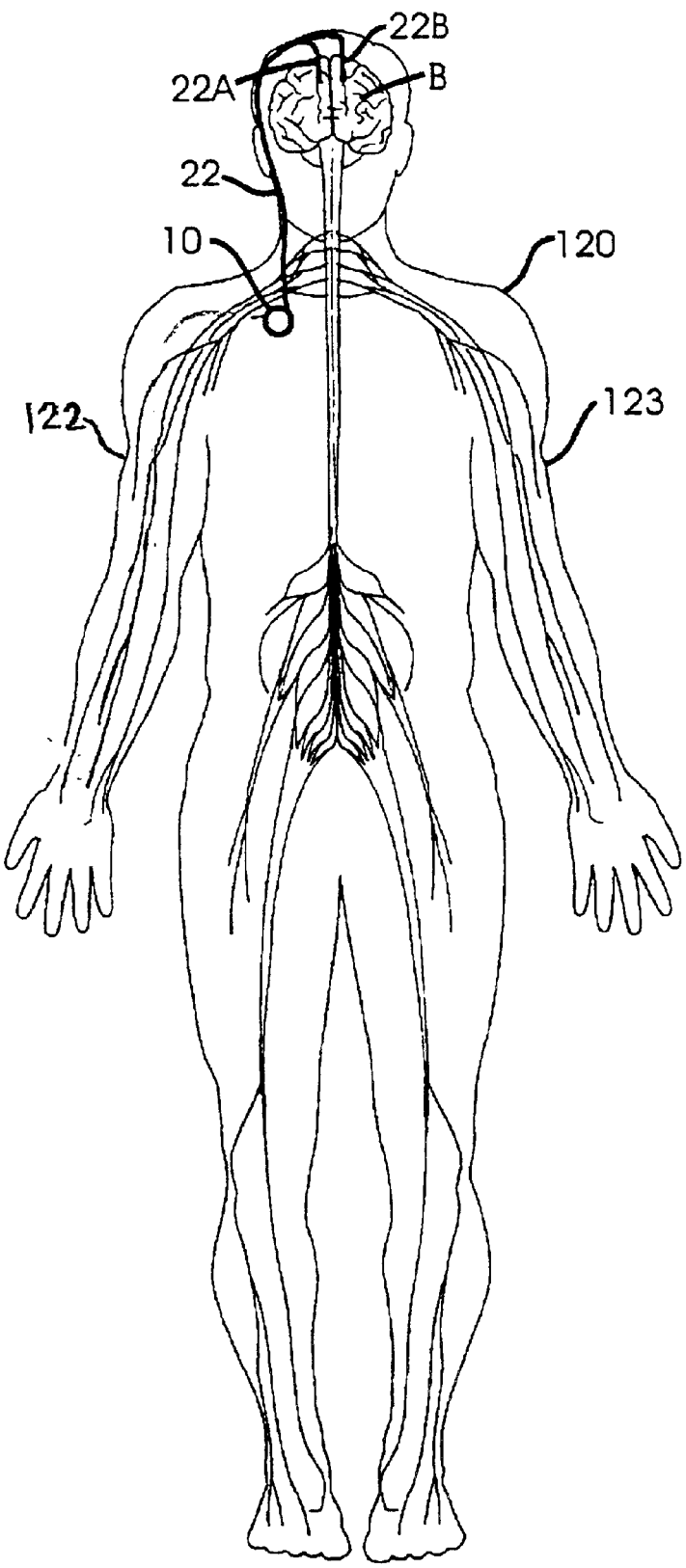
FIG. 1 depicts a neurostimulation device in accordance with an embodiment of the present invention.

FIG. 1 depicts a neurostimulation device 10 in accordance with an embodiment of the present invention. Device 10 made in accordance with the preferred embodiment is preferably implanted below the skin of a patient or, alternatively, may be an external device. Device 10 may be implanted as shown in FIG. 1, in the abdomen or any other portion of the body. A lead 22A is positioned to stimulate a specific site in a brain (B). Device 10 may take the form of a modified signal generator Model 7424 manufactured by Medtronic, Inc. under the trademark Itrel II. Lead 22A may take the form of any of the leads sold with the Model 7424, for stimulating the brain, and is coupled to device 10 by a conventional conductor 22. Alternatively, lead 22A may be any lead suitable for stimulation of a spinal cord. Lead 22A may include a paddle lead, a lead having recording and stimulation electrodes, or a combination catheter/lead capable of providing electrical stimulation and drug delivery.

As shown in FIG. 1, the distal end of lead 22A terminates in one or more stimulation electrodes generally implanted into a portion of the brain by conventional stereotactic surgical techniques. Any number of electrodes may be used for various applications. Each of the electrodes is individually connected to device 10 through lead 22A and conductor 22. Lead 22A is surgically implanted through a hole in the skull and conductor 22 is implanted between the skull and the scalp. Conductor 22 is joined to implanted device 10 in the manner shown.

Conductor 22 may be divided into twin leads 22A and 22B that are implanted into the brain bilaterally as shown. Alternatively, lead 22B may be supplied with stimulating pulses from a separate conductor and signal generator. Leads 22A and 22B could be two electrodes in 1) two separate nuclei that potentiate each other's effects or 2) nuclei with opposite effects with the stimulation being used to fine tune the response through the application of one stimulation pattern to one cite and the application of another stimulation pattern to the other cite.

FIG. 2 is a schematic block diagram of the circuitry of device or signal generator 10 in accordance with a preferred embodiment of the present invention. As preferred, signal generator includes a timer 201 coupled to a microprocessor or a controller 200. Timer 201 establishes when the system is "on" or "off." When implanted, timer 201 is calibrated to turn the stimulation device "on" or "off" in accordance with predetermined counts of timer 201. The operator or patient may calibrate timer 201 such that signal generator 10 is "on" at a specific time in the morning right before the patient usually wakes up and is "off" at a specific time in the evening after the patient has fallen asleep. This calibration may be accomplished during the implantation of signal generator 10. As preferred, timer 201 may be remotely calibrated to adjust for changing time conditions or preferences of the patient (such as changing sleep habits). The additional components of signal generator 10 are discussed in further detail herein.

Figure 3:
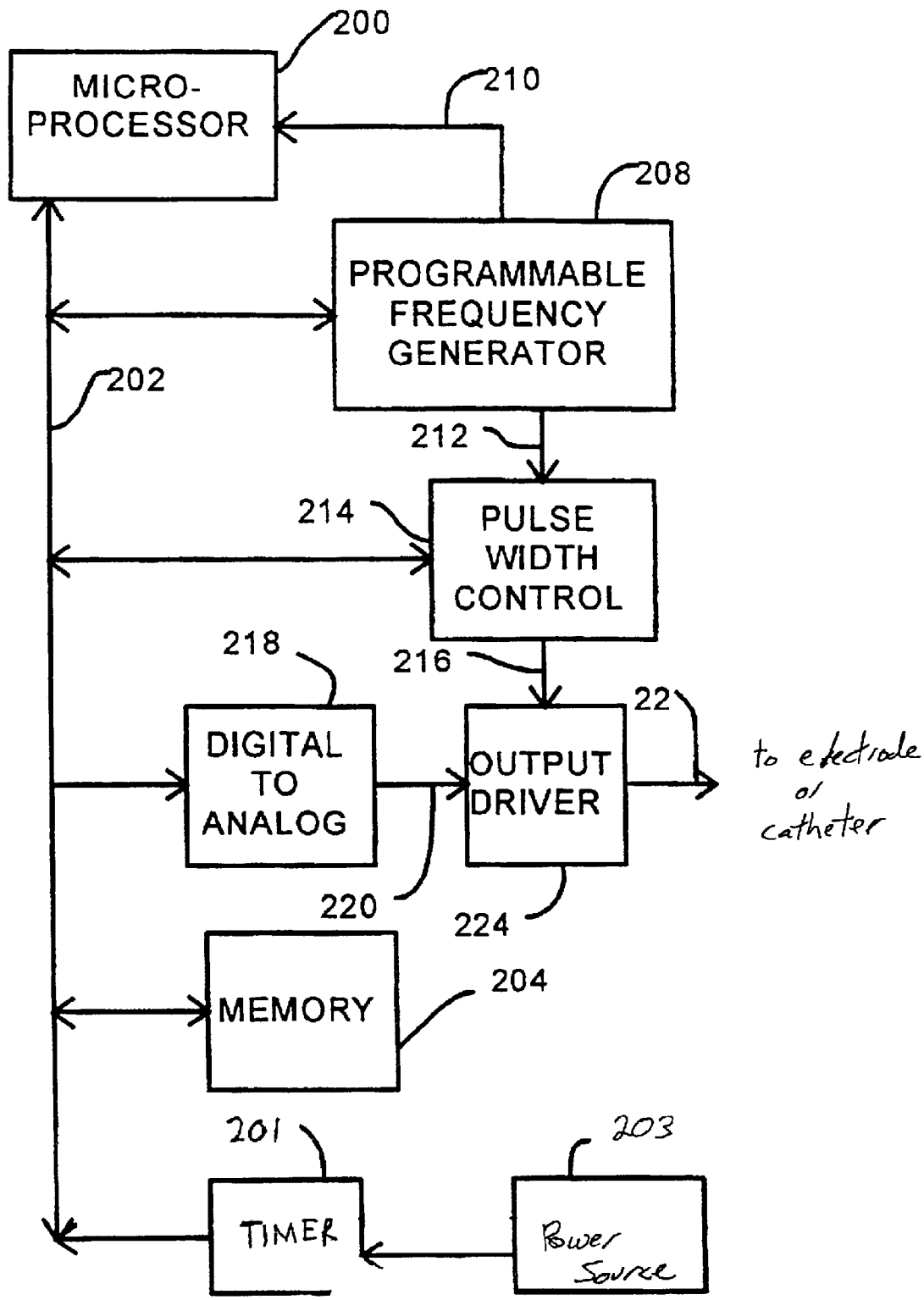
FIG. 3 illustrates a schematic block diagram of another embodiment of signal generator wherein timer is coupled to a power source such as battery of signal generator.

FIG. 3 illustrates a schematic block diagram of another embodiment of signal generator 10 wherein timer 201 is coupled to a power source 203 such as battery of signal generator 10. During "off" periods, timer 201 disconnects power source 203 from providing any electrical energy to signal generator 10. During the "on" stage, timer 201 reconnects power source 203 to provide electrical energy to signal generator 10. Operation of signal generator 10 during the "on" stage may be handled under techniques known in the art.

In yet another embodiment of the present invention, timer 201 may be a real time clock. Clock may be adjusted manually such as, for example, by a switch 230 (FIG. 2A), thus the patient may access via telemetry or, alternatively, clock may be responsive to an external source, such as a wristwatch or a central satellite, to ensure that the clock is timed properly. Advantageously under the latter embodiment, clock may be periodically adjusted to reflect the accurate time-of-day. As such, changes due to daylight savings time changes as well as changes in time zones (if the patient is traveling outside of his/her time zone) may be automatically accounted.

Figure 4:
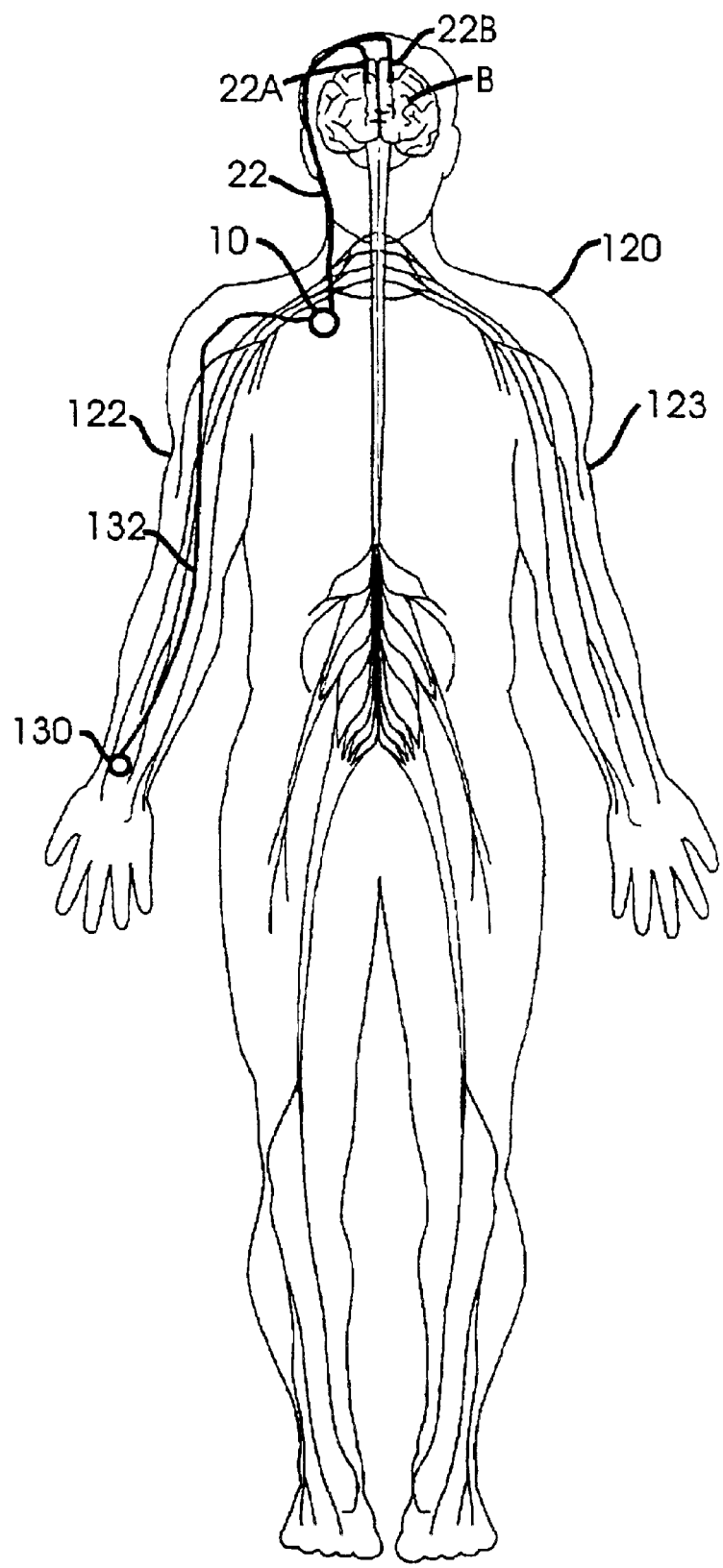
FIG. 4 discloses another embodiment of the present invention wherein a sensor provides feedback as to whether the patient is awake or asleep to determine whether signal generator should be turned on or off.

FIG. 4 discloses another embodiment of the present invention wherein a sensor 130 provides feedback as to whether the patient is awake or asleep to determine whether signal generator 10 should be turned on or off. In one embodiment, sensor 130 may sense a condition of a patient indicating whether the patient is asleep such as whether the eyes are closed, the breathing patterns, or the heart rate. Advantageously, device 10 shuts on or off in response to any number of physical, biological and/or chemical rhythms of the body indicative of whether the patient is sleeping. For example, the system may sense whether the patient's eyes shut for an extended period of time signifying that the patient is napping, sleeping or resting. Alternatively, the system may monitor activity or motion, heart rate, or respiration. Other chemical characteristics may also be monitored to determine whether the treatment therapy should be stopped such as oxygen partial pressure, carbon dioxide concentration, or glucose and insulin concentrations. These characteristics may be measured, for example, in the blood stream or other bodily fluid. Any type of sensor may be used to sense the above characteristics of the body. More detailed description of sensor 130 and other examples of sensors are disclosed in U.S. Pat. No. 5,716,377 entitled "Method of Treating Movement Disorders By Brain Infusion," issued on Feb. 10, 1998 and assigned to Medtronic, Inc., which is incorporated herein by reference in its entirety. Other such sensors are also disclosed in U.S. Pat. Nos. 5,683,422; 5,702,429; 5,713,923; 5,716,316; 5,792,186; 5,814,014; and 5,824,021, all of which are incorporated herein by reference in their entireties.

Signal generator 10 may be automatically turned on or off if any of the conditions sensed by sensor 130 indicates that the patient is sleeping. Sensor 130 may be used in conjunction with or as an alternative to timer 201 (or a real time clock). If used in conjunction with timer 201, signal generator 10 may operate with a default of being "off" at night and a default of being "on" during the day. The default is determined by timer 201. During the day, device 10 may shut off only when a certain threshold of characteristics are sensed by sensor 130 such that it is clear that the patient is asleep. At night when the patient is normally asleep, device 10 may be turned on only when sensor 130 senses characteristics that clearly indicate that the patient has awaken. Sensor 130 provides information to signal generator 10 to determine whether to deviate from the default. These threshold parameters may be adjusted by the physician or the patient. The patient may also have the capability to manually turn on or off signal generator 10 as provided in the art.

Sensor 130 may also be used to provide closed-loop feedback control of the treatment therapy during periods when device 10 is in operation. Alternatively, one or more additional sensors may be implemented for feedback control. The additional sensor is attached to or implanted into a portion of a patient's body suitable for detecting symptoms of a disorder being treated, such as a movement disorder or ischemic pain. The additional sensor is adapted to sense an attribute of the symptom to be controlled or an important related symptom. For motion disorders that result in abnormal movement of an arm, such as arm 122, sensor may be a motion detector implanted in arm 122 as shown in FIG. 4. Such feedback control techniques are disclosed in the patents described above.

Referring to FIG. 4, the output of sensor 130 is coupled by cable 132 to signal generator 10. Alternatively, the output of an external sensor would communicate with signal generator 10 via telemetry. In the embodiment of FIG. 4, sensor 130 monitors heart rate and optionally movement.

Figure 5:
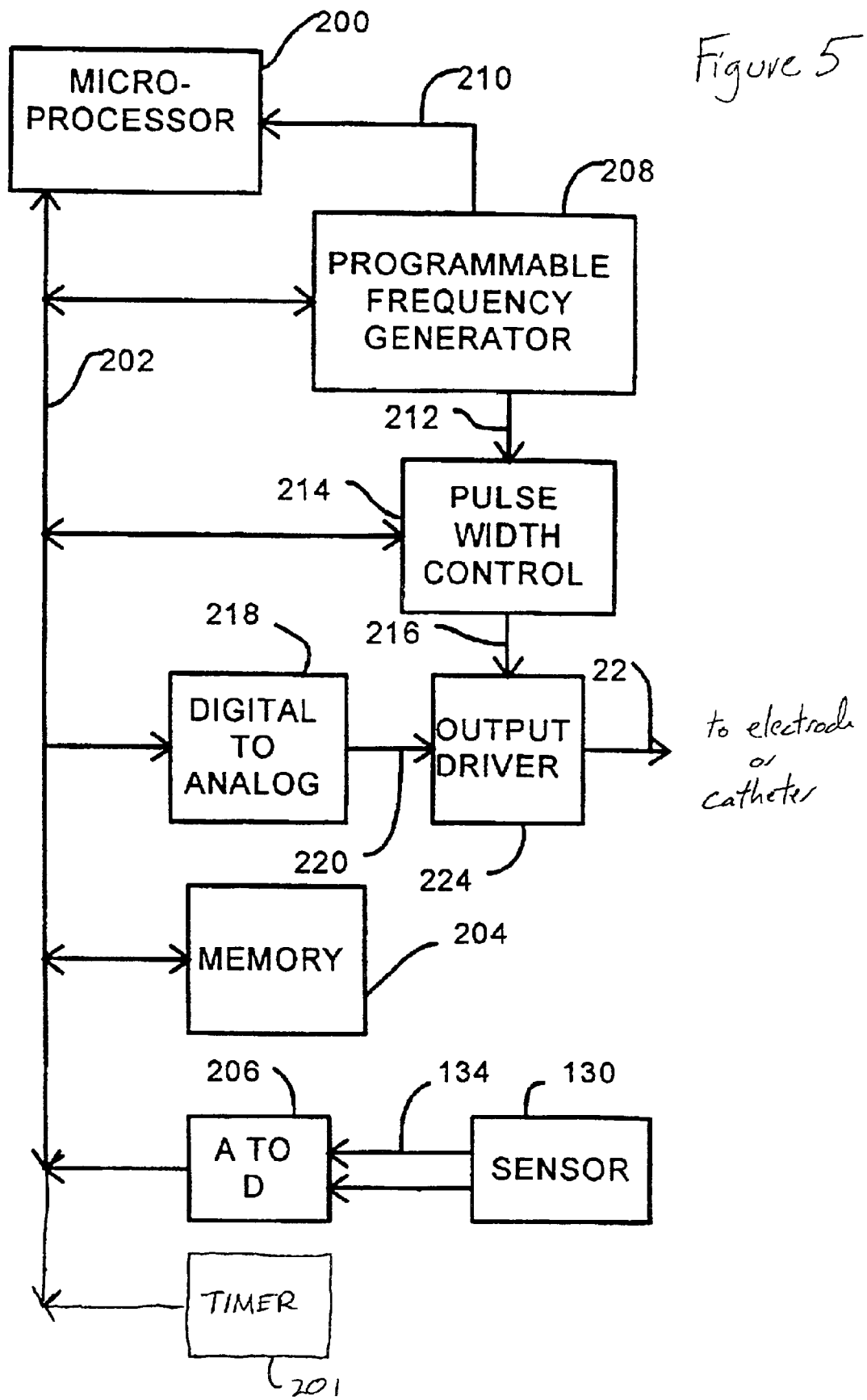
FIG. 5 illustrates a schematic block diagram of the signal generator of FIG. 2 including a sensor signal input from sensor.

FIG. 5 illustrates a schematic block diagram of the signal generator 10 of FIG. 2 including a sensor signal input from sensor 130. Sensor 130 is coupled to an analog to digital converter 206 of signal generator 10. The output of the analog to digital converter 206 is connected to a microprocessor 200 through a peripheral bus 202 including address, data and control lines. Depending upon the particular sensor signal used, an analog to digital converter would not be necessary. The output from sensor 130 can be filtered by an appropriate electronic filter in order to provide a control signal for signal generator 10.

Microprocessor 200 is coupled to timer 201 to receive timing information and to sensor 130 to receive patient information. Microprocessor 200 may then responsively determine whether the treatment therapy should be turned on or off. Other componentry of signal generator 10 is shown to generate the desired signal pulsing parameters and/or to provide feedback control of the treatment therapy. The present invention may be practiced without microprocessor 200. For example, a controller or electrical circuitry having the desired functionality may be implemented in place of microprocessor 200 to receive the timer and/or sensor information and process the information to determine whether treatment therapy is to be delivered.

Figure 6:
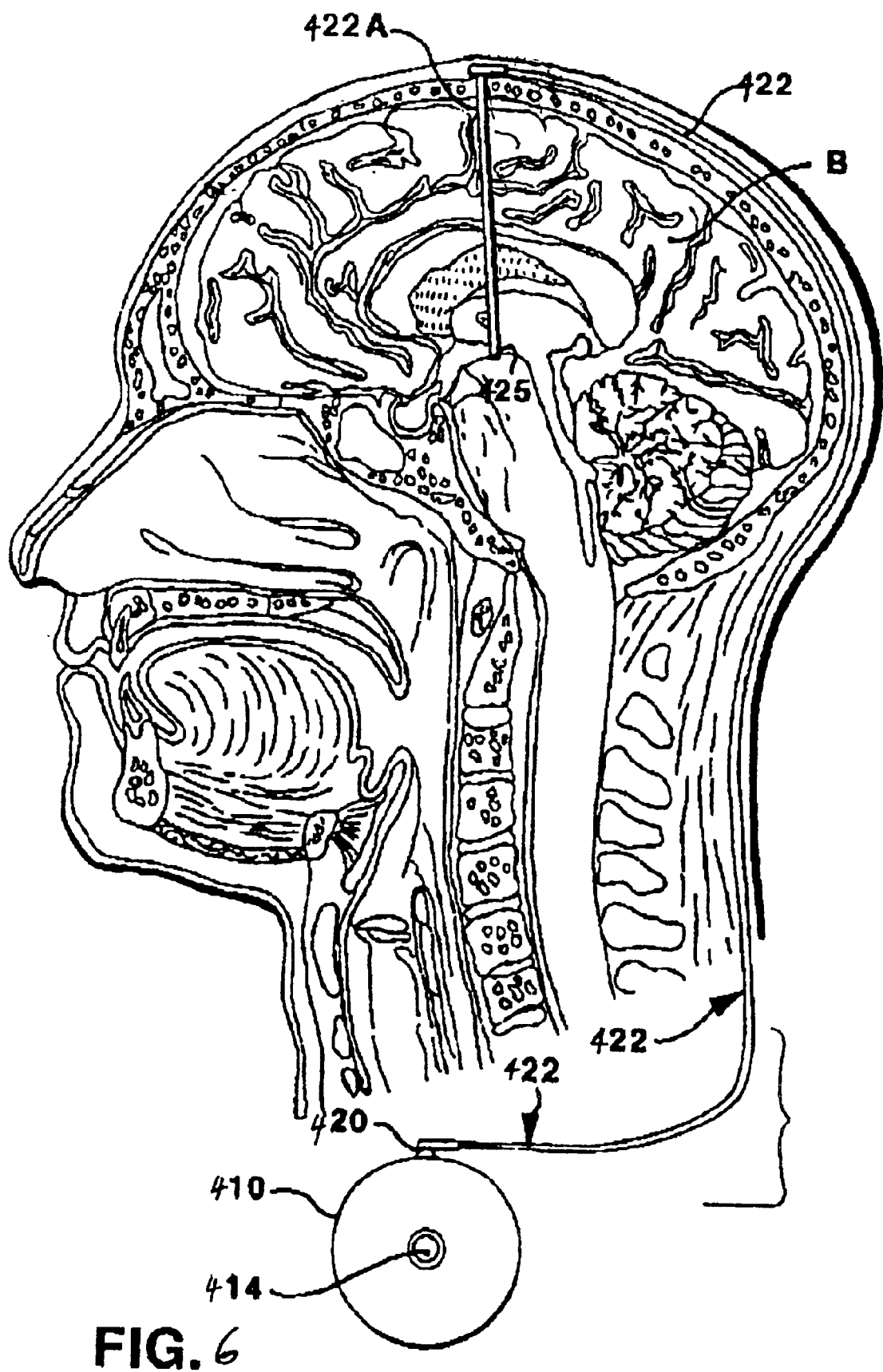
FIG. 6 depicts a drug infusion system in accordance with an embodiment of the present invention.

The present invention is equally suitable for use in drug infusion systems to automatically provide or cease providing drug therapy to a patient. As shown in FIG. 6, the drug infusion system includes a pump 410 having at least one reservoir for storing at least one drug. The drug may be delivered via a catheter 422. Catheter 422 may be coupled to a single tube 422A or tube 422A may be divided into twin tubes, tube 422A and a second tube (not shown), that are implanted into the brain bilaterally. The second tube may supply drugs from a second catheter and pump or may supply drugs from catheter 422 to a second location within the brain B. Such drug infusion systems that may incorporate the present invention are disclosed in U.S. Pat. Nos. 5,711,316; 5,713,923; 5,735,814; and 5,782,798, each of which are incorporated herein by reference in their entireties. The drug pump may include similar componentry as that of the signal generators 10 discussed in FIGS. 2, 3 and 5.

Advantageously, the present invention may be utilized in a number of different treatment therapies, including, but not limited to, treatment of pain, movement disorders and other neurological disorders such as epilepsy, to provide a mechanism to automatically turn off treatment therapy during periods that it is not required or necessary. As used herein, the term disorder includes any disorder, illness or maladies. Additionally, the present invention may automatically turn on the treatment therapy during or right before the patient requires the treatment therapy.

Those skilled in that art will recognize that the preferred embodiments may be altered or amended without departing from the true spirit and scope of the invention, as defined in the accompanying claims.

I claim:

1. A drug delivery system device for treatment of a disorder comprising in combination:
   (a) an implantable pump having at least one reservoir for storing at least one drug;
   (b) a real time clock coupled to the pump and providing time-of-day information to establish whether the pump is to deliver the drug;
   (c) at least one implantable catheter coupled to the pump and adapted to deliver the drug to at least one predetermined site in a body of a patient; and
   (d) a sensor coupled to the pump for generating a signal indicative of whether a patient is asleep or awake, wherein the pump is responsive to the signal.

2. A drug delivery system of claim 1, further comprising:
   (e) an analog-to-digital converter coupling the sensor to the pump.

3. In an implanted drug delivery device for treatment of a disorder having an implantable pump and at least one implantable catheter coupled to the pump, a method of automatically starting and stopping delivery of treatment therapy to a patient comprising the steps of:
   (a) calibrating the implantable pump with at least two parameters for determining whether treatment is to be delivered, a first parameter corresponding to a first time of day indicating that the therapy is to be started and a second parameter corresponding to a second time of day indicating that the therapy is to be stopped;
   (b) monitoring a timer to determine whether at least one of the parameters is satisfied;
   (c) if the first parameter is satisfied, automatically initiating the implantable pump to start delivering drug treatment therapy to the patient; and
   (d) if the second parameter is satisfied, automatically initiating the implantable pump to stop the delivery of the drug treatment therapy.

4. A method of claim 3, wherein a third parameter corresponds to a pattern indicative of whether the patient is asleep or awake and further comprising the step of:
   (e) if the third parameter indicates that the patent is awake, automatically initiating the implantable pump to start delivering drug treatment therapy to the patient; and
   (f) if the third parameter indicates that the patient is asleep, automatically initiating the implantable pump to stop the delivery of the drug treatment therapy.

5. A method of claim 3, wherein the disorder is selected from the group consisting of pain, movement disorder and epilepsy.

6. A system for automatically starting and stopping delivery of treatment therapy to a patient comprising in combination:
   (a) an implantable pump;
   (b) at least one implantable catheter coupled to the implantable pump and adapted to deliver at least one drug to at least one site in a body of a patient;
   (c) a timer providing timing information; and
   (d) means responsive to the timer for causing the implantable pump to start delivering drug treatment therapy to the patient if the timing information satisfies a first time of day parameter and for causing the implantable pump to stop delivering drug treatment therapy to the patient if the timing information satisfies a second time of day parameter.

7. The system of claim 6, wherein the means is a microprocessor.

8. The system of claim 6, wherein the means is a controller.

9. The system of claim 6, wherein the means is circuitry.

10. The system of claim 6, wherein the timer is a real time clock.

11. The system of claim 10, wherein the real time clock is configured to receive input from an external source to provide time of day information.

12. The system of claim 6, further comprising:
   (e) a sensor coupled to the implantable pump for generating a signal indicative of whether a patient is asleep or awake.

13. The system of claim 6, further comprising:
   (e) a switch coupled to the implantable pump and responsive to input by a patient to allow the patient to manually turn off the device.

14. A system for automatically starting and stopping delivery of treatment therapy to a patient comprising in combination:
   (a) an implantable pump;
   (b) at least one implantable catheter coupled to the implantable pump and adapted to deliver the drug treatment therapy to at least one site in a body of a patient;
   (c) a sensor that provides information as to whether the patient is asleep or awake; and
   (d) means responsive to the sensor for causing the implantable pump to start delivering drug treatment therapy if the patient is awake and for causing the implantable pump to stop delivering drug treatment therapy if the patient is asleep.

15. The system of claim 14, wherein the means is a microprocessor.

16. The system of claim 14, wherein the means is a controller.

17. The system of claim 14, wherein the means is circuitry.

18. The system of claim 14, wherein the sensor is coupled to the implantable pump utilizing an analog-to-digital converter.

19. The system of claim 14, further comprising:
   (e) a real-time clock coupled to the implantable pump for providing timing information.

20. The system of claim 19, wherein the real time clock is configured to receive input from an external source to provide time of day information.

21. The system of claim 14, further comprising:
   (e) a switch coupled to the signal generator and responsive to input by a patient to allow the patient to manually turn off the device.

22. A method of automatically starting and stopping delivery of treatment therapy to a patient with an implantable pump having at least one implantable catheter coupled to the implantable pump, comprising the steps of:
   (a) sensing by a sensor a characteristic of the patient to determine whether the patient is awake or asleep;
   (b) if the sensor indicates that the patient is awake, causing the implantable pump to start delivering drug treatment therapy to the patient; and
   (c) if the sensor indicates that the patient is asleep, causing the implantable pump to stop delivering drug treatment therapy to the patient.

23. The method of claim 22, wherein the step of sensing includes the step of sensing motion by the patient.

24. The method of claim 22, wherein the step of sensing includes the step of sensing a heart rate of the patient.

25. The method of claim 22, wherein the step of sensing includes the step of sensing respiration of the patient.

26. The method of claim 22, wherein the step of sensing includes the step of sensing a chemical characteristic of the patient.

27. The method of claim 22, wherein the step of sensing includes the step of sensing a chemical characteristic of the patient selected from the group consisting of oxygen partial pressure, carbon dioxide concentration, glucose concentration, and insulin concentration.

28. The method of claim 22, wherein the step of sensing includes the step of sensing whether eyes of the patient are open or closed.

* * * * *

UNITED STATES PATENT AND TRADEMARK OFFICE
CERTIFICATE OF CORRECTION

PATENT NO. : 6,923,784 B2
DATED : August 2, 2005
INVENTOR(S) : Marc T. Stein

It is certified that error appears in the above-identified patent and that said Letters Patent is hereby corrected as shown below:

Column 6,
Line 42, should read -- (e) if the third parameter indicates that the patient is --.

Signed and Sealed this

Fourteenth Day of February, 2006

JON W. DUDAS
*Director of the United States Patent and Trademark Office*